United States Patent [19]

Evers et al.

[11] 4,120,900

[45] Oct. 17, 1978

[54] FLUOROCARBON BIS(O-AMINOPHENOL) COMPOUNDS CONTAINING A HYDROCARBON MOIETY

[75] Inventors: Robert C. Evers, Dayton; Tonson Abraham, Kettering, both of Ohio

[73] Assignee: The United States of America as represented by the Secretary of the Air Force, Washington, D.C.

[21] Appl. No.: 856,385

[22] Filed: Dec. 1, 1977

[51] Int. Cl.$^2$ ............... C07C 91/44; C08G 23/00; C08G 65/40
[52] U.S. Cl. .................. 260/571; 528/205; 528/210
[58] Field of Search ............. 260/571, 47 R, 61

[56] References Cited

U.S. PATENT DOCUMENTS

| | | | |
|---|---|---|---|
| 3,306,876 | 2/1967 | Kantor et al. | 260/47 R |
| 3,846,376 | 11/1974 | Evers | 260/61 |
| 3,903,166 | 9/1975 | Evers | 260/571 |
| 3,994,861 | 11/1976 | Evers | 260/61 |
| 4,005,142 | 1/1977 | Evers | 260/571 |

*Primary Examiner*—Winston A. Douglas
*Assistant Examiner*—John J. Doll
*Attorney, Agent, or Firm*—Joseph E. Rusz; Cedric H. Kuhn

[57] ABSTRACT

Fluorocarbon bis(o-aminophenol) compounds in which fluoroalkylene groups attached to each aminophenol radical are separated by a hydrocarbon moiety. The compounds are useful as monomers in preparing thermooxidatively and hydrolytically stable, low glass transition temperature perfluoroalkylene ether bibenzoxazole polymers containing hydrocarbon cure sites.

3 Claims, No Drawings

FLUOROCARBON BIS(O-AMINOPHENOL) COMPOUNDS CONTAINING A HYDROCARBON MOIETY

RIGHTS OF THE GOVERNMENT

The invention described herein may be manufactured or used by or for the Government of the United States for all governmental purposes without the payment of any royalty.

FIELD OF THE INVENTION

This invention relates to fluorocarbon bis(o-aminophenol) compounds containing a hydrocarbon moiety. In one aspect it relates to a process for preparing the compounds.

BACKGROUND OF THE INVENTION

Perfluoroalkylene ether bibenzoxazole polymers can be synthesized that possess a combination of high thermooxidative stability, low glass transition temperatures, and hydrolytic stability. Because of these desirable properties, the polymers have shown promise as candidate materials for advanced aerospace applications. Examples of such polymers are disclosed by R. C. Evers, one of the coinventors herein, in U.S. Pat. Nos. 3,846,376; 3,994,861; and 4,005,142. Although the polymers can be cured to elastomers, the process is difficult and requires relatively extreme conditions. Additionally, the mechanical properties of the resultant elastomers often require upgrading in order to be useful in aerospace applications.

It is an object of this invention, therefore, to provide monomers that can be used in the synthesis of perfluoroalkylene ether bibenzoxazole polymers containing hydrocarbon cure sites.

Another object of the invention is to provide fluorocarbon bis(o-aminophenol) compounds containing a hydrocarbon moiety.

A further object of the invention is to provide a process for synthesizing the fluorocarbon bis(o-aminophenol) compounds.

Other objects and advantages of the invention will become apparent to those skilled in the art upon consideration of the accompanying disclosure.

SUMMARY OF THE INVENTION

The present invention resides in a bis(o-aminophenol) compound having the following structural formula:

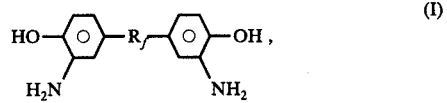

where $R_f$ is $(CF_2)_3-(CH_2)_2-(CF_2)_3$ or $(CF_2)_3CH=CH(CF_2)_3$. The compounds are characterized by containing hydrocarbon groups which, when incorporated in a polymer chain or background, function as cure sites.

In one embodiment, the invention lies in a four-stage process for synthesizing the bis(o-aminophenol) compounds. The reaction involved in the synthesis can be represented by the following equations:

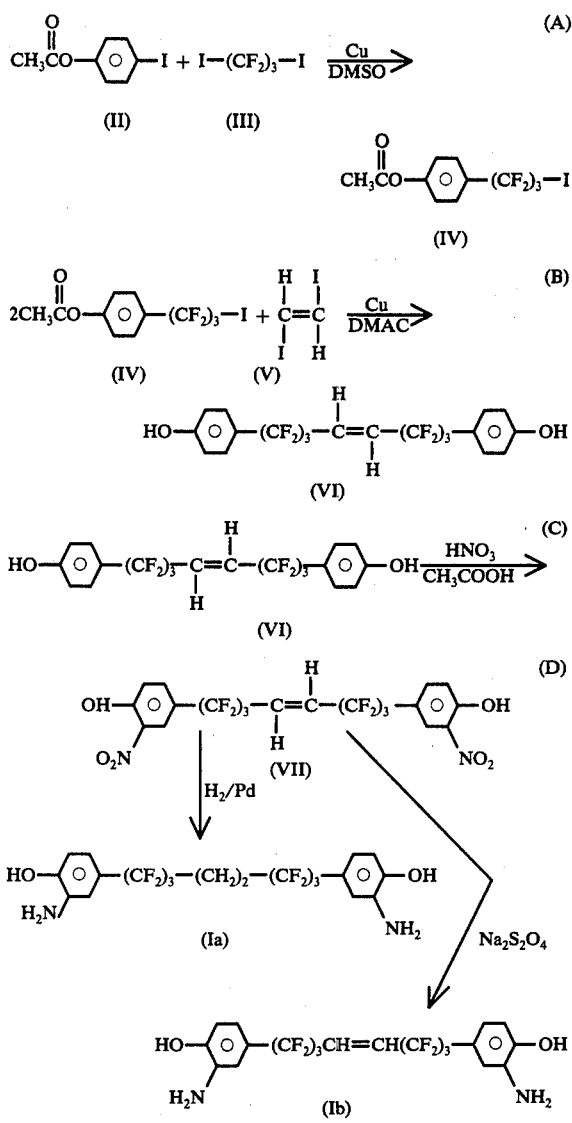

The first stage of the process (equation A) involves reacting p-iodophenyl acetate (II) with 1,3-diiodohexafluoropropane (III). The reaction is conducted in anhydrous dimethyl sulfoxide (DMSO) in the presence of copper powder. Equimolar amounts of the reactants can be used, but it is usually preferred to employ an excess of the diiodohexafluoropropane e.g., 1 to 1.5 moles per mole of the acetate. For every mole of acetate, at least 2, e.g., about 2 to 10, gram atoms of copper are utilized. The reaction is carried out in an inert atmosphere at a temperature ranging from about 110° to 130° C. Examples of gases suitable for providing an inert atmosphere include nitrogen, helium and argon. The reaction period usually ranges from about 2 to 5 hours. At the end of the reaction period, the reaction product is recovered from the reaction mixture. In a preferred procedure, the reaction mixture is allowed to cool after which saturated aqueous ammonium chloride and methylene chloride are added. The excess copper and cuprous salts are then filtered off, and the organic layer is separated. After extracting the aqueous layer with additional methylene chloride, the organic extracts are combined, washed with water, dried over anhydrous magnesium sulfate, and finally reduced in volume to a light yellow oil. The oil is refluxed in acetic anhydride for about 30 minutes to one hour followed by removal of excess acetic anhydride and acetic acid by vacuum distillation. Distillation of the residual oil yields crude 4-(perfluoro-3-iodopropyl)phenyl acetate (IV) which is then purified by recrystallization from hexane.

In the second stage of the process (equation B), copper powder is added to a solution of 4-(perfluoro-3-iodopropyl)phenyl acetate (IV) and trans-1,2-diiodoethylene (V) in anhydrous dimethylacetamide (DMAC). The reaction is carried out in an inert atmosphere at a temperature ranging from about 110° to 130° C. for a period of about 8 to 16 hours. The mole ratio of compound (IV) to compound (V) is 2 to 1 while about 3 to 5 gram atoms of copper per mole of compound (IV) are added. At the end of the reaction period, the reaction product is recovered. In the recovery it is preferred to follow a procedure similar to that described in the preceding paragraph. Thus, after adding saturated aqueous ammonium chloride and methylene chloride to the cooled reaction mixture, the excess copper and cuprous salts are removed by filtration. The organic layer is then separated, and the aqueous layer is extracted with additional methylene chloride. The organic extracts are combined and washed with 15 percent hydrochloric acid followed by a thorough washing with water. Drying of the organic phase over anhydrous magnesium sulfate followed by evaporation of the extract yields a crude light brown solid. The solid is added to methanol and then refluxed for about 0.5 to 1.5 hours after addition of concentrated hydrochloric acid. Extraction of the cold methanol solution with methylene chloride followed by evaporation of the solvent after washing with water and drying over anhydrous magnesium sulfate yields a solid which can be recrystallized from a methylene chloride-hexane mixture. Trans-1,2-[3-(4-hydroxyphenyl)perfluoropropyl]ethylene (VI) is obtained in the form of white crystals.

The third stage of the process (equation C) is conducted by dissolving trans-1,2-[3-(4-hydroxyphenyl)-perfluoropropyl]ethylene (VI) in acetic acid. After adding concentrated nitric acid to the solution, the solution is stirred at 45° to 55° C. until an exotherm occurs in from 5 to 10 minutes. During the exotherm, the temperature is maintained at about 60° C. After stirring at 55° to 60° C. for 4 to 5 hours, a precipitate appears that increases as stirring is continued. The precipitate is recovered by filtration, washed with pentane, and dried to give trans-1,2-[3-(4-hydroxy-3-nitrophenyl)perfluoropropyl]ethylene (VII).

In the fourth stage of the process (equation D), when it is desired to prepare 1,2-[3-(4-hydroxy-3-aminophenyl)perfluoropropyl]ethane (Ia), a solution of trans-1,2-[3-(4-hydroxy-3-nitrophenyl)perfluoropropyl]ethylene (VII) in ethyl acetate containing 10 percent palladium on charcoal is deoxygenated with nitrogen. Thereafter, the solution is pressurized with hydrogen for 3 to 10 hours at room temperature. After filtering off the catalyst, the ethyl acetate solution is reduced in volume and crystallization is induced by adding hexane to the hot solution. Compound (Ia) is obtained as a product in the form of white crystals.

When it is desired to obtain olefinic product (Ib), sodium dithionite in water is added at room temperature to a solution of the bis(o-nitrophenol) (VII) in methanol. After adding water, the resultant white slurry is extracted several times with ether. The combined ether extracts are then dried over anhydrous magnesium sulfate and stripped to dryness under reduced pressure to give a white residue. The solid is dissolved in hot toluene which is treated with charcoal and then reduced in volume. Cooling of the solution gives olefinic product (Ib) in the form of white platelets.

The compounds of this invention are useful as monomers in preparing thermooxidatively and hydrolytically stable, low glass transition temperature perfluoroalkylene ether bibenzoxazole polymers containing hydrocarbon cure sites. The polymers are synthesized by the polycondensation of a compound of this invention with a long chain fluorocarbon ether diimidate ester. A more complete discussion of the preparation of the polymers is contained in our copending application Ser. No. 863,026, filed on Dec. 21, 1977, the disclosure of which is incorporated herein by reference.

A more comprehensive understanding of the invention can be obtained by referring to the following illustrative examples which are not intended, however, to be unduly limitative of the invention.

EXAMPLE I (A) Preparation of 4-(Perfluoro-3-iodopropyl)phenyl acetate

A solution of p-iodophenyl acetate (27.5 g, 105 mmol) and 1,3-diiodohexafluoropropane (52.0 g, 128.7 mmol) in 100 ml of anhydrous dimethyl sulfoxide was heated to 120° C. under nitrogen. Copper powder (13.5 g, 211 g atoms) was added to the vigorously stirred solution in five approximately equal amounts at 20 minute intervals. After the addition of copper was complete, the reaction mixture was stirred at 120° C. for an additional 1.5 hours. On cooling, saturated aqueous ammonium chloride together with methylene chloride was added to the reaction vessel. The excess copper and cuprous salts were filtered off, the organic layer was separated, and the aqueous layer was extracted with more methylene chloride. The organic extracts were combined, washed well with water, dried over anhydrous magnesium sulfate, and reduced in volume to a light yellow oil. The oil was refluxed in 25 ml of acetic anhydride for 45 minutes and the excess acetic anhydride and acetic acid were vacuum distilled. Distillation of the residual oil yielded 24.85 g of crude 4-(perfluoro3-iodopropyl)-phenyl acetate, bp 126°-127° C./3.4 mm Hg, mp 75°-81° C. Recrystallization of this material from hexane gave 20.8 g (48% yield) of purer material, mp 84.5°-88° C. Repeated crystallization from hexane raised the melting point to 88.5°-89.5° C., which could not be improved upon by further recrystallization.

Analysis Calc'd for $C_{11}H_7F_6IO_2$: C,31.37; H,1.71; I,30.79. Found: C,32.33; H,1.28; I,30.09.

The product was identified by infrared and nuclear magnetic resonance spectroscopy as 4-(perfluoro-3-iodopropyl)phenyl acetate. Molecular weight (mass spectroscopy):

Calc'd —412. Found — 412.

(B) Preparation of Trans-1,2-[3-(4-hydroxyphenyl)perfluoropropyl]ethylene

Copper powder (10.0 g) was added to a solution of 4-(perfluoro-3-iodopropyl)phenyl acetate (15.0 g, 36.4 mmol) and trans-1,2-diiodoethylene (5.25 g, 18.7 mmol) in 90 ml of anhydrous dimethyl acetamide. The reaction mixture was maintained under nitrogen at 120° C. for 12 hours with vigorous stirring. Saturated aqueous ammonium chloride and methylene chloride were then added to the cooled reaction mixture. The excess copper and cuprous salts were filtered off, the organic layer separated, and the aqueous layer extracted with more methylene chloride. The organic extracts were combined, washed with 15% hydrochloric acid followed by a thorough washing with water. Drying of the organic phase over anhydrous magnesium sulfate followed by evaporation of the extract yielded a crude light brown solid. This solid was taken up in 95 ml of methanol and refluxed for 1 hour after the addition of 5 ml of concentrated hydrochloric acid. Extraction of the cold methanol solution with methylene chloride followed by evaporation of the solvent after washing with water and drying over anhydrous magnesium sulfate yielded a solid which could be recrystallized from methylene chloride-hexane. Trans-1,2-[3-(4-hydroxyphenyl)perfluoropropyl]ethylene (6.02 g) was obtained in 65% yield as white crystals, mp 134°–137.5° C. Crystals with mp 137.5–138° C. could not be further purified by recrystallization.

Analysis calc'd for $C_{20}H_{12}F_{12}O_2$: C,46.88; H,2.36. Found : C,47.29; H,1.62.

The product was identified by infrared and nuclear magnetic resonance spectroscopy as trans-1,2-[3-(4-hydroxyphenyl)perfluoropropyl]ethylene.

Molecular weight (mass spectroscopy): Calc'd - 512. Found - 512.

(C) Preparation of Trans-1,2-[3-(4-hydroxy-3-nitrophenyl)perfluoropropyl]ethylene Trans-1,2-[3-(4-hydroxyphenyl)perfluoropropyl]ethylene (5.66 g) was warmed in 20 ml of acetic acid until a clear solution formed. After the addition of concentrated nitric acid (4.0 ml), the reaction solution was stirred at 45°–55° C. until an exotherm occurred after 5–10 minutes of heating. During the exotherm the temperature was maintained at 60° C. (ice bath). The red color that developed during this period gradually faded to a light yellow color on continued stirring at 55°–60° C. for 4.5 hours. The precipitate that appeared, however, increased as stirring continued. The acetic acid was then chilled (ice bath), the light yellow precipitate filtered off, washed with pentane and dried to give 5.06 g (75% yield) of trans-1,2-[3-(4-hydroxy-3-nitrophenyl)-perfluoropropyl]ethylene, mp 122°–123° C. This melting point could not be improved by recrystallization from methylene chloride-hexane soltions.

Analysis Calc'd for $C_{20}H_{10}F_{12}N_2O_6$: C,39.88; H,1.67; N,4.65. Found : C,40.29; H,0.92; N,5.05.

The product was identified by infrared and nuclear magnetic resonance spectroscopy as trans-1,2-[3-(4-hydroxy-3-nitrophenyl)perfluoropropyl]ethylene.

Molecular weight (mass spectroscopy): Calc'd — 602. Found — 602.

(C) Preparation of 1,2-[3-(4-Hydroxy-3-aminophenyl)perfluoropropyl]ethane

A solution of trans-1,2-[3-(4-hydroxy-3-nitrophenyl)-perfluoropropyl]ethylene (5.0 g) in 60 ml of ethyl acetate containing 10% palladium on charcoal (1.0 g) was deoxygenated with nitrogen and subjected to 50 psi of hydrogen, with agitation, for 5 hours at room temperature. After filtering off the catalyst, the ethyl acetate solution was reduced in volume and crystallization induced by adding hexane to the hot ethyl acetate solution. 1,2-[3-(4-hydroxy-3-aminophenyl)perfluoropropyl]ethane was obtained as white crystals in two fractions: 1.97 g, d 202–202.5C (sealed cap) and 0.98 g, d 202° C. (sealed cap). Total yield: 59%. The higher melting material could not be further purified by recrystallization.

Analysis Calc'd for $C_{20}H_{16}F_{12}N_2O_2$: C,44.29; H,2.60; N,5.16. Found: C,44.28; H,2.61; N,4.75.

The product was identified by infrared and nuclear magnetic resonance spectroscopy as 1,2-[3-(4-hydroxy-3-aminophenyl)perfluoropropyl]ethane.

Molecular weight (mass spectroscopy): Calc'd — 544. Found — 544.

EXAMPLE II

Preparation of 1,2-[3-(4-Hydroxy-3-aminophenyl)perfluoropropyl-]ethylene

Sodium dithionite (10 g) in 30 ml of water was added slowly with stirring at room temperature to a solution of 1.0 g (0.0017 mole) of trans-1,2-[3-(4-hydroxy-3-nitrophenyl)perfluoropropyl]ethylene (prepared as described in Example I) in 250 ml of methanol. The methanolic solution turned bright yellow and then slowly faded to water-white as reduction occurred. After addition of the sodium dithionite was completed, stirring continued for an additional 30 minutes at which time water was added resulting in a total solution volume of 750 ml. The resultant white slurry was extracted three times with 200 ml portions of ether and the combined ether extracts were washed repeatedly with water. The ether solution was then dried over anhydrous magnesium sulfate and stripped to dryness under reduced pressure to give a white residue. Most of this solid was soluble in 900 ml of hot toluene which was treated with charcoal and reduced in volume to 100 ml. Cooling in dry ice gave 0.5 g (55% yield) of the olefinic product as white platelets, mp 187°–188° C.

Analysis Calc'd for $C_{20}H_{14}F_{12}N_2O_2$: C,44.29; H,2.60; N,5.16 Found: C,44.85; H,2.79; N,4.99.

Molecular weight (mass spectroscopy): Calc'd — 542. Found — 542.

EXAMPLE III

A run was carried out in which a perfluoroalkylene ether bibenzoxazole polymer was synthesized by the polycondensation of the fluorocarbon ether bis(o-aminophenol) as prepared in Example I with a fluorocarbon ether thioimidate ester. The reaction involved is shown by the following equation:

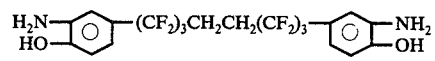

(1)

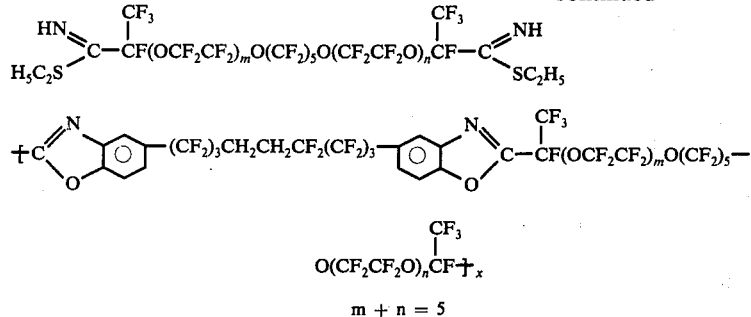

$$+C \underset{O}{\overset{N}{\diagdown}} \underset{}{\overset{}{\bigcirc}} -(CF_2)_3CH_2CH_2CF_2(CF_2)_3 - \underset{O}{\overset{N}{\diagdown}} \underset{}{\overset{}{\bigcirc}} C - \overset{CF_3}{\underset{|}{CF}}(OCF_2CF_2)_mO(CF_2)_5-$$

$$O(CF_2CF_2O)_n\overset{CF_3}{\underset{|}{CF}}\}_x$$

m + n = 5

In conducting the run, 5 ml of redistilled hexafluoroisopropanol was added to a mixture of the fluorocarbon bis(o-aminophenol) (1) (0.229 g, 0.00042 mole) and the thioimidate ester (2) (0.521 g, 0.00042 mole). Glacial acetic acid (0.10 g, 0.0016 mole) was added and the resultant suspension stirred under nitrogen at 55°–60° C. After several days a clear amber reaction mixture resulted. After a total reaction time of 10 days, the polymer was precipitated from methanol and redissolved in Freon 113. Drying for 2 hours at 100° C. (0.05 mm Hg) yielded 0.51 g (75% yield) of rubbery polymer ($\eta$ inh = 0.62 dl/g in hexafluoroisopropanol at 25° C.).

Analysis Calc'd: C,30.31; H,0.62; N,1.72. Found: C,30.81; H,0.31; N,1.90.

Thermogravimetric analysis in air indicated an onset of breakdown at 380° C. with a 25 percent weight loss at 500° C. Differential scanning calorimetry revealed a glass transition temperature at −14° C. No change in polymer infrared spectrum was observed after exposure to 95 percent relative humidity at 200° F. for several weeks. Admixture of a small portion of the polymer with a 1/1 benzoyl peroxidemagnesium oxide formulation (about 5% by weight) followed by heating at 250° F. for an hour yielded a tough, insoluble, very densely crosslinked vulcanizate.

From the foregoing, it is seen that the fluorocarbon bis(o-aminophenol) compounds of this invention can be used to prepare perfluoroalkylene ether bibenzoxazole polymer that are thermooxidatively and hydrolytically stable and possess a low glass transition temperature. Furthermore, because the polymers contain aliphatic hydrocarbon groups (derived from the bis(o-aminophenol) compounds) which are reactive to free radical catalysis, they can be readily cured under milder conditions than are ordinarily employed.

As will be evident to those skilled in the art, modifications of the present invention can be made in view of the foregoing disclosure without departing from the spirit and scope of the invention.

We claim:

1. A bis(o-aminophenol) compound having the following structural formula:

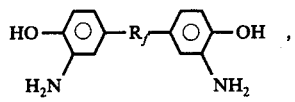

where $R_f$ is $(CF_2)_3-(CH_2)_2-(CF_2)_3$ or $(CF_2)_3CH=CH(CF_2)_3$.

2. The bis(o-aminophenol) compound according to claim 1 in which $R_f$ is $(CF_2)_3-(CH_2)_2-(CF_2)_3$.

3. The bis(o-aminophenol) compound according to claim 1 in which $R_f$ is $(CF_2)_3CH=CH(CF_2)_3$.

* * * * *